US010279013B2

(12) United States Patent
Casebolt et al.

(10) Patent No.: US 10,279,013 B2
(45) Date of Patent: May 7, 2019

(54) METHODS FOR TREATING AN ANIMAL

(71) Applicant: PURETEIN BIOSCIENCE LLC., St. Louis Park, MN (US)

(72) Inventors: Brett Casebolt, Edina, MN (US); Chad D. Hagen, Sleepy Eye, MN (US); Robert Eldon Musser, Good Thunder, MN (US)

(73) Assignee: PURETEIN BIOSCIENCE LLC, St. Louis Park, MN (US)

( * ) Notice: Subject to any disclaimer, the term of this patent is extended or adjusted under 35 U.S.C. 154(b) by 0 days.

(21) Appl. No.: 15/102,601

(22) PCT Filed: Dec. 19, 2014

(86) PCT No.: PCT/US2014/071387
§ 371 (c)(1),
(2) Date: Jun. 8, 2016

(87) PCT Pub. No.: WO2015/095650
PCT Pub. Date: Jun. 25, 2015

(65) Prior Publication Data
US 2016/0317624 A1 Nov. 3, 2016

Related U.S. Application Data

(60) Provisional application No. 61/918,405, filed on Dec. 19, 2013.

(51) Int. Cl.
*A61K 38/30* (2006.01)
*A23K 20/147* (2016.01)
*A61K 9/00* (2006.01)

(52) U.S. Cl.
CPC ............ *A61K 38/30* (2013.01); *A23K 20/147* (2016.05); *A61K 9/0053* (2013.01)

(58) Field of Classification Search
None
See application file for complete search history.

(56) References Cited

U.S. PATENT DOCUMENTS

| | | | | |
|---|---|---|---|---|
| 5,444,045 | A * | 8/1995 | Francis | C07K 14/65 514/4.8 |
| 7,169,963 | B2 * | 1/2007 | Wheeler | A01K 67/0278 800/14 |
| 2005/0215477 | A1 | 9/2005 | Schaffer et al. | |
| 2008/0194553 | A1* | 8/2008 | Gillessen | A61K 31/404 514/233.8 |
| 2010/0173839 | A1 | 7/2010 | Glass | |
| 2011/0152188 | A1 | 6/2011 | Mahler et al. | |
| 2011/0200591 | A1 | 8/2011 | Bisgaard-Frantzen | |
| 2012/0315294 | A1 | 12/2012 | Suradhat et al. | |
| 2013/0331313 | A1 | 12/2013 | Berenson et al. | |
| 2016/0007632 | A1 | 1/2016 | Strohbehn | |

FOREIGN PATENT DOCUMENTS

| | | |
|---|---|---|
| WO | WO 93/25226 A1 | 12/1993 |
| WO | WO 93/25227 A1 | 12/1993 |
| WO | WO 99/56758 A1 | 11/1999 |
| WO | WO 01/62277 A1 | 8/2001 |
| WO | WO 03/030918 A1 | 4/2003 |
| WO | WO 2005/067962 A2 | 7/2005 |
| WO | WO 2007/057748 A2 | 5/2007 |
| WO | WO 2008/016958 A2 | 2/2008 |
| WO | WO 2013/009755 * | 1/2013 |
| WO | WO 2013/050529 A2 | 4/2013 |

OTHER PUBLICATIONS

Walton et al., Progress in Growth Factor Research, 6(2-4):385-395, 1995.*
Roberts et al. Can Vet J, 44:31-37, 2003.*
Ashare et al., "Insulin-like Growth Factor-1 Improves Survival in Sepsis via Enhanced Hepatic Bacterial Clearance," Apr. 22, 2008, *American Journal of Respiratory and Critical Care Medicine*, 178: 149-57.
Baxter, "Insulin-like growth factor (IGF)-binding proteins: interactions with IGFs and intrinsic bioactivities," 2000, *Am J Physiol Endocrinol Metab*, 278: E967-E976.
Benfield et al., "Characterization of Swine Infertility and Respiratory Syndrome (SIRS) Virus (Isolate ATCC VR-2332)," Apr. 1992, *Journal of Veterinary Diagnostic Investigation*, 4(2): 127-133.
Breier et al., "Radioimmunoassay for insulin-like growth factor-I: solutions to some potential problems and pitfalls," Jun. 4, 1990. *Journal of Endocrinology* (1991), 128:347-57.
Carel et al., "Safety of Recombinant Human Growth Hormone" in *Current Indications for Growth Hormone Therapy*, $2^{nd}$ rev. ed., Karger (Ed.). Hindmarsh PC: Switzerland; 2010. pp. 40-54.
Collins et. al., "Isolation of swine infertility and respiratory syndrome virus (isolate ATCC VR-2332) in North America and experimental reproduction of the disease in gnotobiotic pigs," Jan. 11, 1992, *Journal of Veterinary Diagnostic Investigation.*, 4(2): 117-126.
Conover, "Regulation and Physiological Role of Insulin-Like Growth Factor Binding Proteins," 1996, *Endocrine Journal*, 43(Suppl):S43-S48.
Daughaday et al., "Insulin-like growth factors I and II. Peptide, messenger ribonucleic acid and gene structures, serum, and tissue concentrations," Feb. 1989, *Endocrine Reviews*, 10(1):68-91.
Daughaday et al., "Serum somatomedin binding proteins: Physiologic significance and interference in radioligand assay," Mar. 1987, *The Journal of Laboratory and Clinical Medicine*, 109(3):355-63.

(Continued)

*Primary Examiner* — Marianne P Allen
(74) *Attorney, Agent, or Firm* — Mueting, Raasch & Gebhardt, P.A.

(57) ABSTRACT

Provided herein are methods for treating an animal using a composition that includes active IGF. The methods include treating an animal at risk of having an infection caused by an infectious agent, treating an animal having an infection, and treating a symptom associated with an infection. In one embodiment, the infectious agent is a virus. In one embodiment, the administering includes daily administration of at least 0.05 nanograms of active IGF-1 per kilogram bodyweight of the animal daily (ng/kg), at least 0.1 ng/kg, at least 2 ng/kg, at least 5 ng/kg, or at least 10 ng/kg.

9 Claims, 1 Drawing Sheet

(56) References Cited

OTHER PUBLICATIONS

Holtkamp et al., "Assessment of the economic impact of porcine reproductive and respiratory syndrome virus on United States pork producers," Jul. 18, 2012, *Journal of Swine Health and Production* (2013), 21(2):72-84.

Hwa et al., "The Insulin-Like Growth Factor-Binding Protein (IGFBP) Superfamily," 1999, *Endocrine Reviews*, 20(6):761-87.

Karney et al., "Differential Responsiveness of Human Breast Cancer Cell Lines MCF-7 and T47D to Growth Factors and 17 β-Estradiol," 1988, *Cancer Research*, 48:4083-92.

Wensvoort et al., "Mystery swine disease in The Netherlands: the isolation of Lelystad Virus," Jul. 1991, *The Veterinary Quarterly*, 13 (3): 121-130.

\* cited by examiner

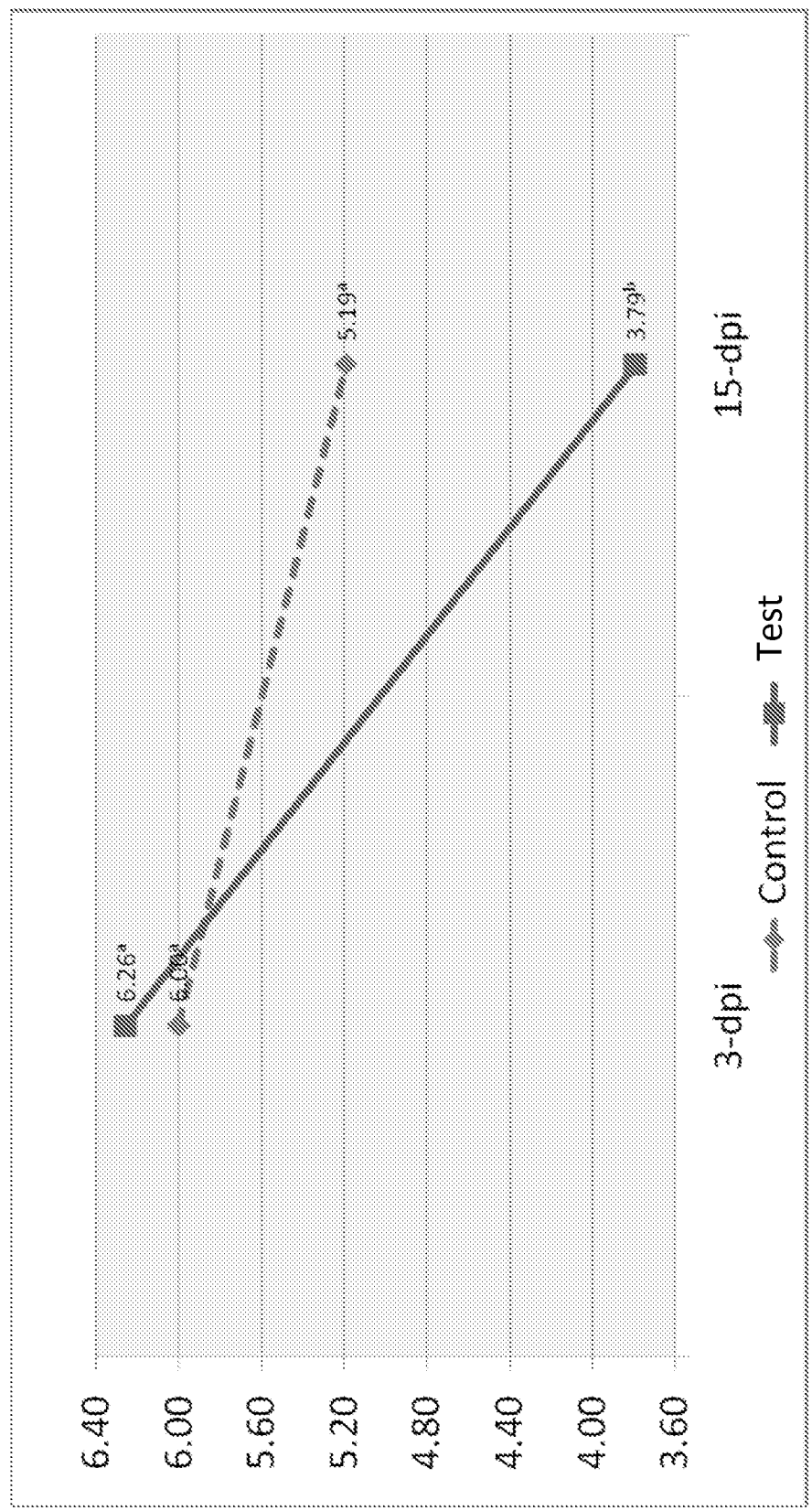

METHODS FOR TREATING AN ANIMAL

CROSS-REFERENCE TO RELATED APPLICATIONS

This application is the § 371 U.S. National Stage of International Application No. PCT/US2014/071387, filed Dec. 19, 2014, which claims the benefit of U.S. Provisional Application Ser. No. 61/918,405, filed Dec. 19, 2013, which are incorporated by reference herein.

BACKGROUND

Viral diseases have a significant impact on livestock throughout the world. Porcine reproductive and respiratory syndrome virus (PRRSV) is the causative agent of a disease characterized by respiratory disorders in young pigs and reproductive failure in sows (Benfield et al., 1992, *J. Vet. Diagn. Invest.*, 4:127-133, Collins et. al., 1992, *J. Vet. Diagn. Invest.*, 4:117-126, Wensvoort et al., 1991, *Vet. Q.*, 13:121-130) and is now endemic in most countries. The disease is characterized by reproductive failure in pregnant sows and respiratory problems in pigs of all ages. The disease has a significant economic impact on the swine industry, and in the United States is estimated to result in economic loses of $664 million per year (Holtkamp et al., 2013, J Swine Health Prod., 21(2):72-84).

SUMMARY OF THE APPLICATION

Provided herein are methods for treating an animal at risk of having an infection caused by an infectious agent, such as a virus. In one embodiment, the method includes administering active IGF to an animal at risk of having an infection caused by an infectious agent, wherein the risk of having an infection is decreased compared to a control animal that is not administered the composition.

Also provided are methods for treating an animal having an infection. In one embodiment, the method includes administering active IGF to an animal having an infection caused by an infectious agent, wherein the composition includes active IGF-1, wherein the administering results in reducing the amount of infectious agent in the animal.

Also provided herein are methods for treating a symptom associated with an infection. In one embodiment, the method includes administering an effective amount of a composition to an animal having an infection caused by an infectious agent, wherein the composition includes active IGF-1, wherein a symptom of the infection is reduced.

In one embodiment, the administering includes oral administration of the active IGF, such as by administration of a feed to the animal.

In one embodiment, the administering includes daily administration of at least 0.05 nanograms of active IGF-1 per kilogram bodyweight of the animal daily (ng/kg), at least 0.1 ng/kg, at least 2 ng/kg, at least 5 ng/kg, or at least 10 ng/kg.

In one embodiment, the infectious agent is a virus, such as an enveloped virus or a non-enveloped virus. Examples of an enveloped virus include a member of the family Arteriviridae, a member of the family Orthomyxoviridae, and a member of the family Coronaviridae. Examples of a member of the family Arterivirdae include a porcine reproductive and respiratory syndrome virus (PRRSV), an equine arteritis virus, and a simian haemorrhagic fever virus. Examples of a member of the family Orthomyxoviridae include Influenzavirus A, Influenzavirus B, and Influenzavirus C. Examples of a member of the family Coronaviridae include a coronavirus, a togovirus, and a porcine epidemic diarrhea virus. Examples of a non-enveloped virus include a member of the family Adenoviridae, such as a member of the genus *Mastadenovirus*.

In one embodiment, the IGF-1 administered to the subject is obtained from a natural source that has been processed to increase the amount of active IGF-1. The natural source may be blood or a blood-derived product, milk or a milk-derived product, or colostrum or a colostrum-derived product.

In one embodiment, the administering also includes administering inactive IGF-1, wherein at least 20%, wherein at least 30%, or wherein at least 40% of the total IGF-1 administered is active IGF-1.

In one embodiment, the animal is a vertebrate, such as a mammal or an avian species. Examples of mammals include a bovine species, a porcine species, a cervid species, a canine species, a feline species, an equine species, an ovine, and a human. In one embodiment, the animal is an adult, and in one embodiment, the animal is an age between birth and weaning The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, and such examples can be used in various combinations. In each instance, the recited list serves only as a representative group and should not be interpreted as an exclusive list.

BRIEF DESCRIPTION OF THE FIGURES

FIG. 1. Quantitative Real-Time PCR. Dpi, days-post-inoculation. Y axis, log RNA copies/ml.

DETAILED DESCRIPTION OF ILLUSTRATIVE EMBODIMENTS

Provided herein are methods for using a composition that includes one or more proteins. In one embodiment, a composition includes insulin-like growth factor (IGF), such as IGF-1 and/or IGF-2. IGFs play a role in both regulation of normal physiology, as well as a number of pathological states, including cancer, and play a role in cell proliferation and inhibition of cell death. IGF may affect different growth stages. Insulin-like growth factor 2 (IGF-2) is thought to be a primary growth factor required for early development while insulin-like growth factor 1 (IGF-1) expression is required for achieving maximal growth. Almost every cell in the human body is affected by IGF-1, especially cells in muscle, cartilage, bone, liver, kidney, nerves, skin, and lungs. IGF-1 can also regulate cell growth and development, especially in nerve cells, as well as DNA synthesis. IGFs are highly conserved between species, and the amino acid sequences of IGFs from different species are known and readily available to the skilled person.

Whether a protein is an IGF can be easily determined by the skilled person. For instance, polyclonal and monoclonal antibodies that specifically bind to IGF-1 and/or to IGF-2 are commercially available, and react with IGF from various species including human, equine, canine, bovine, porcine, and avian. These readily available antibodies lack cross-reactivity and/or interference by other closely related proteins and binding proteins. A single antibody or a panel of antibodies that recognizes different regions of an IGF, such as N-terminal, C-terminal, or amino acids present between the ends of the protein, may be used to determine whether a protein is an IGF protein. Methods for determining the activity of an IGF protein including IGF-1 or IGF-2 are known in the art are routine.

IGFs are proteins with high sequence similarity to insulin, but unlike insulin, IGFs associate with distinct binding proteins present in serum and other biological fluids (Baxter, 2000, Am J Physiol Endocrinol Metab, 278: E967-E976; Hwa et al., 1999, Endocrine Reviews, 20(6):761-787). Most IGF present in products derived from an animal, such as, but not limited to, blood and blood-derived products, milk and milk-derived products, and colostrum and colostrum-derived products, is bound to a binding protein. However, since these binding proteins inhibit the activity of IGF, most IGF present in animal derived products is inactive due to its being bound to a binding protein. For instance, less than 1% of IGF-1 in plasma is not bound to a binding protein (Carel et al., Safety of Recombinant Human Growth Hormone, In: Current Indications for Growth Hormone Therapy, 2nd rev. ed., vol. ed.: Hindmarsh, Karger, Switzerland, page 48).

A composition useful in the methods described herein includes active IGF, and optionally includes inactive IGF. In one embodiment, a composition is present in a food product. As used herein, a "food product" is a compound or mixture of compounds that can be ingested by a subject. A food product may be solid, semi-solid, or liquid. Examples include, but are not limited to, solid and semi-solid dairy products, including fermented dairy products, for instance yogurt. Beverages to which IGF can be added include milk, vegetable juice, fruit juice, soy milk, soybean milk, fermented soybean milk, and fruit flavored dairy beverages. In one embodiment, a food product is a feed for animal use, for instance, for feeding domesticated animals such as companion animals including, but not limited to, dogs or cats, and livestock including, but not limited to, bovine, porcine, avian, cervid, canine, feline, equine, or ovine animals. The appropriate concentration to add to a food product can be determined by the skilled person having knowledge of the level of active IGF in a composition and the approximate amount of food product to be eaten daily by the animal. In those embodiments where the animal is not a human, the skilled person will understand that estimating the amount of feed eaten by an animal is typically based on the average for a population of animals.

IGF useful in the methods described herein is obtainable from various sources. In one embodiment, a source is biological material from an animal. Examples of animals include, but are not limited to, vertebrates. Examples of vertebrates include, but are not limited to, mammals, such as a species that is bovine, porcine, cervid, canine, feline, equine, ovine, or a human. Another example of a vertebrate is an avian species. Examples of biological materials include, but are not limited to, blood and blood-derived products (e.g., whole blood, red blood cells, plasma, and derivatives thereof); milk and milk products (e.g., liquid milk, powdered milk, cheese, whey and whey products, curd, cheese, casein, lactose, and derivatives thereof); colostrum and colostrum-derived products (e.g., liquid colostrum, dried colostrum); egg and egg-derived products (e.g., egg yolk, egg whites, egg membranes), bodily fluids (e.g., saliva, semen), and tissues (e.g., mucosa tissue, intestinal tissue, embryonic tissue). Examples of plasma include, but are not limited to, dried plasma and liquid plasma and fractions thereof, such as a lipid fraction. Examples of whey products include, but are not limited to, liquid whey, whey protein concentrate, whey protein isolate, whey cream, whey retentate, procream, deproteinized whey, delactosed permeate. Examples of colostrum-derived products include, but are not limited to, liquid colostrum whey, colostrum whey protein concentrate, colostrum whey protein, colostrum whey cream, colostrum whey retentate, colostrum procream, colostrum deproteinized whey, colostrum delactosed permeate, colostrum casein, colostrum lactose, colostrum curd. In one embodiment, the colostrum is colostrum secreted by a female within the first 6, the first 12, the first 24, or the first 48 hours after birth of offspring. In one embodiment, a natural source of IGF useful in the methods described herein is not colostrum. In one embodiment, IGF useful in the methods described herein is produced using recombinant techniques, or chemically or enzymatically synthesized. As used herein, IGF from a natural source, for instance, blood or a blood-derived product, is not produced using recombinant techniques, or chemically or enzymatically synthesized. Biological material, such as blood or a blood-derived product, useful for producing a composition with active IGF is readily available commercially.

A biological material may be enriched for the amount of total IGF present. A protein is enriched if it is present in a significantly higher fraction compared to the biological material from which the protein was enriched. The higher fraction may be, for instance, an increase of 2-fold, 4-fold, 6-fold, 10-fold, 100-fold, 1,000-fold, or 10,000-fold. Enrichment may result from reducing the amount of other molecules present in the biological material, e.g., proteins. However, the term enriched does not imply that there are no other molecules, e.g., proteins, present. Enriched simply means the relative amount of IGF has been significantly increased. The term "significant" indicates that the level of increase is useful to the person making such an increase. Enrichment of IGF is the result of intervention by a person to elevate the proportion of the protein.

Optionally, IGF can be purified from a biological material. A protein is considered to be purified if at least 75%, least 85%, or at least 95% of other components present in the biological material are removed. Proteins that are produced through chemical or recombinant means are considered to be purified. Methods for enriching and/or purifying IGF are known to the skilled person and are routine. Non-limiting examples of such procedures include fractionation on immunoaffinity or ion-exchange columns; ethanol precipitation; reverse phase HPLC; chromatography on silica or on an ion-exchange resin such as DEAE; chromatofocusing; SDS-PAGE; ammonium sulfate precipitation; gel filtration using, for example, cross-linked gels and/or hollow fiber; and ligand affinity chromatography.

In one embodiment, a composition may include a pharmaceutically acceptable carrier. As used herein "pharmaceutically acceptable carrier" includes, but is not limited to, saline, solvents, dispersion media, coatings, antibacterial and antifungal agents, isotonic and absorption delaying agents, and the like, compatible with pharmaceutical administration.

A composition compatible with pharmaceutical administration may be prepared by methods well known in the art of pharmacy. In general, a composition can be formulated to be compatible with its intended route of administration. A formulation may be solid or liquid. Administration may be systemic or local. In some aspects local administration may have advantages for site-specific, targeted disease management. Local administration may provide high, clinically effective concentrations directly to the treatment site, with less likelihood of causing systemic side effects.

Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of a composition described herein includes tablets, capsules or liquids, as well as a food product. Appropriate dosage forms for parenteral administration may include intravenous administration. Appropriate dosage forms for topical administration may include creams, ointments, and skin patch. Methods for making a pharmaceutically acceptable composition that includes IGF are known to the skilled person (Mahler et al., US Published Patent Application 20110152188).

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., the IGF, such as IGF-1) in the required amount in an appropriate solvent with one or a combination of ingredients, as required, followed by filtered sterilization. Generally, dispersions are prepared by incorporating the active compound into a sterile vehicle, which contains a basic dispersion medium and any other appropriate ingredients. In the case of sterile powders for the preparation of sterile injectable solutions, preferred methods of preparation include vacuum drying, spray-drying, and freeze-drying to yield a powder of the active ingredient plus any additional desired ingredient from a previously sterilized solution thereof.

A composition for use in topical administration may be formulated into many types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, or pastes (Williams, Transdermal and Topical Drug Delivery, Pharmaceutical Press, London, 2003). Variations and other vehicles will be apparent to the skilled artisan and are appropriate for use in the methods described herein.

It is also contemplated that an active compound may be encapsulated for delivery past the rumen of a ruminant or to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed, examples include nanospheres and nanocapsules) that can be used as delivery vehicles to deliver such ingredients to skin or digestive tract.

Oral compositions generally include an inert diluent or an edible carrier. In one embodiment, an oral composition includes a food product. For the purpose of oral therapeutic administration, the active compound can be incorporated with excipients and used in the form of tablets, troches, or capsules, e.g., gelatin capsules. Oral compositions can also be prepared using a fluid carrier for administering a liquid to an animal, such as inclusion of active IGF in an animal's water supply or use with an oral syringe. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can also be prepared in the form of suppositories (e.g., with conventional suppository bases such as cocoa butter and other glycerides) or retention enemas for rectal delivery.

Pharmaceutical administration can be one or more times per day to one or more times per week, including once every other day. The skilled artisan will appreciate that certain factors may influence the dosage and timing required to effectively treat a subject, including, but not limited, to the severity of the infection, previous treatments, the general health and/or age of the subject, and other diseases present.

Most, e.g., 95% to 99%, of the IGF obtained from many natural sources is associated with binding protein that causes the IGF to be inactive. Optionally, the amount of active IGF in a composition that is obtained from a natural source can be increased, e.g., the amount of total IGF in the composition may be unchanged but the amount of active IGF is increased, such that the amount of active IGF as a percentage of the total IGF is increased. Methods for increasing the amount of IGF that is active include processes routinely used to activate functional proteins obtained from a biological material. Such processes include, but are not limited to, exposing the biological material to heat shock, temperature adjustment, alcohol extraction, pH adjustment, enzyme addition, ionic changes, other chemical additions, and pressure, or combinations thereof (Daughaday et al., 1989, Endocr Rev. 10:68-91; Daughaday et al., 1987, J Lab Clin Med. 109:355-363; Breier et al., 1991, J Endocrinol. 128:347-357). Without intending to be limited by theory, such methods typically cause the dissociation of the binding protein from the IGF protein.

In one embodiment, the amount of active IGF in a composition that is obtained from a natural source can be increased by at least 2-fold, at least 4-fold, at least 5-fold, at least 10-fold, at least 20-fold, at least 50-fold, or at least 100-fold compared to the amount of active IGF in the composition before it is processed to activate IGF. In one embodiment, at least 20%, at least 30%, at least 40%, at least 50%, at least 60%, at least 70%, at least 80%, at least 90%, or 100% of the total IGF present is active. In one embodiment, no greater than 80%, no greater than 70%, no greater than 60%, no greater than 50%, no greater than 40%, no greater than 30%, no greater than 20%, no greater than 10%, or no greater than 5% of the total IGF present is inactive (e.g., bound to a binding protein). The composition subjected to the processing can be, for instance, a biological material from an animal, such as a blood or blood-derived product. Optionally, the biological material may be one that has been enriched for total IGF. Products made from natural sources and processed to activate IGF are commercially available as the product BETAGRO and IMMUTEIN (GBH Labs, Maple Grove, Minn.).

In those embodiments where the source of IGF is a biological source, the composition may typically include other components, including other proteins.

An IGF is considered to be active if it is not bound to a binding protein, and is considered to be inactive if it is bound to a binding protein. Active IGF is often referred to in the art as free, unbound, bioactive, and active. Methods for measuring the concentration of active IGF are known to the skilled person and are routine. Assays are commercially available, including solid phase sandwich ELISA assays that specifically measure IGF that is not bound to a binding protein (e.g., R&D Systems, catalog number DFG100).

Also provided herein are methods for using a composition described herein. In one embodiment, the method includes treating an animal. In one embodiment, the method is for treating an infection in an animal. The method includes administering an effective amount of a composition that includes active IGF as described herein to an animal having, or at risk of having, an infection. Optionally, the method includes determining whether the number of infectious agent causing the infection has decreased. As used herein, the term "infection" refers to the presence of an infectious agent in an animal's body, which may or may not be clinically apparent.

In one embodiment, the method is for treating a symptom in an animal. The method includes administering an effective amount of a composition to a subject having or at risk of having a condition, or exhibiting symptoms and/or clinical signs of a condition. Optionally, the method includes determining whether at least one symptom and/or clinical sign of the condition is changed, preferably, reduced.

Treatment of an infection, symptoms, and/or clinical signs associated with an infection can be prophylactic or, alternatively, can be initiated after the development of an infection. As used herein, the term "symptom" refers to subjective evidence of the infection experienced by the subject and caused by an infectious agent. As used herein, the term "clinical sign" or, simply, "sign" refers to objective evidence of disease or condition caused by an infection. Symptoms and/or clinical signs associated with an infection and the evaluations of such symptoms vary depending upon the infectious agent, and are routine and known in the art. For instance, examples of conditions and/or clinical signs caused by a porcine reproductive and respiratory syndrome virus (PRRSV) include reproductive failure in sows such as abortions and giving birth to stillborn or mummified fetuses, fever, labored breathing, decreased mobility, decreased eating, decreased milk production, and cyanosis of the ear and vulva. In neonatal pigs, the disease causes respiratory distress, with increased susceptibility to respiratory infections such as Glasser's disease.

Treatment that is prophylactic, for instance, initiated before a subject manifests symptoms or signs of an infection, is referred to herein as treatment of a subject that is "at risk" of developing the infection. Thus, typically, an animal "at risk" of developing an infection is an animal present in an area where animals having the condition have been diagnosed and/or is likely to be exposed to the infectious agent causing the condition even if the animal has not yet manifested symptoms or signs of any condition caused by the infectious agent. Accordingly, administration of a composition can be performed before, during, or after the subject has first contact with the infectious agent, or the occurrence of the conditions associated with the infectious agent. Treatment initiated after the subject's first contact with the infectious agent may result in decreasing the infection by the infectious agent, completely removing the infection, and/or decreasing the likelihood of experiencing a clinically evident infection compared to an animal to which the composition is not administered. Treatment initiated after the development of a condition may result in decreasing the severity of the symptoms of the infection, or completely removing the symptoms. In one embodiment, an animal is immuno-compromised, and in one embodiment, and animal is not immuno-compromised.

In one embodiment, the administering can be feeding a composition that includes active IGF to the animal. In one embodiment, active IGF can be present in a food product. The food product may naturally include the active IGF, or the food product may be supplemented with active IGF. In one embodiment, the addition of active IGF occurs by the supplementation of a food product with a biological material, such as a blood-derived product, e.g., plasma, that has been processed to increase the amount of active IGF. The amount of active IGF administered by feeding on a daily basis may be at least 0.05 ng/kg, at least 0.1 ng/kg, at least 0.5 ng/kg, at least 2 ng/kg, at least 5 ng/kg, at least 10 ng/kg, at least 20 ng/kg, at least 50 ng/kg, or at least 100 ng/kg, where ng refers to nanograms of active IGF and kg refers to kilograms bodyweight of the animal. In one embodiment, the amount of active IGF administered by feeding on a daily basis may be no greater than 150,000 ng /kg, no greater than 100,000 ng /kg, no greater than 50,000 ng/kg, or no greater than 20,000 ng/kg, where ng refers to nanograms of active IGF and kg refers to kilograms bodyweight of the animal. The active IGF administered may be active IGF-1, active IGF-2, or a combination thereof. In one embodiment, the active IGF administered is active IGF-1. In one embodiment there is no upper limit on the amount of active IGF administered.

In one embodiment, the feed may be provided to an animal while it is exhibiting signs and/or symptoms of infection. In one embodiment, the feed may be provided to an animal for at least 1 day, at least 4 days, at least 7 days, at least 2 weeks, at least 3 weeks, at least 1 month, at least 2 months, or at least 3 months. In one embodiment, the feed may be provided to an animal for no greater than 3 months, no greater than 2 months, no greater than 1 month, no greater than 3 weeks, or no greater than 2 weeks. Thus, in one embodiment, the period of time may be at least 1 day and no greater than three months, or any combination of time periods selected between those numbers.

In one embodiment, the administering can be parenteral or topical. The amount of active IGF to be administered by a parenteral or topical route in the methods described herein can be determined by standard pharmaceutical procedures in cell cultures or experimental animals, e.g., for determining the $ED_{50}$ (the dose therapeutically effective in 50% of the population). The data obtained from cell culture assays and animal studies can be used in formulating a range of dosage for use in an animal. The dosage of active IGF lies preferably within a range that includes the $ED_{50}$ with little or no toxicity; however, it is expected that high levels of active IGF will not be detrimental to an animal. The dosage may vary within this range depending upon the dosage form employed and the route of administration utilized. For a compound used in the methods of the invention, the therapeutically effective dose can be estimated initially from cell culture assays and/or experimental animals.

Examples of animals include, but are not limited to, vertebrates. Examples of vertebrates include, but are not limited to, mammals, such as a species that is bovine (such as a domesticated cow), porcine (such as a domesticated pig, e.g., a sow), cervid (such as a deer), canine (such as a domesticated dog), feline (such as a domesticated cat), equine (such as a domesticated horse), ovine, or a human. Another example of a vertebrate is an avian species (such as domesticated fowl, e.g.,. broiler chicken, egg laying hen, turkey). The animal may be at an age that is between birth and weaning, between post-weaning and adulthood, or a mature (adult) animal. The animal may be a female or a male.

Examples of infectious agents include viruses. A virus may be an enveloped or a non-enveloped virus. Examples of viruses include, but are not limited to, a member of the order Nidovirales. Examples of this order include members of the family Arterivirdae and members of the family Coronaviridae. Members of the family Arterivirdae include members of the genus *Arterivirus*. Examples of *Arterivirus* include porcine reproductive and respiratory syndrome virus (PRRSV), equine arteritis virus, and simian haemorrhagic fever virus. Examples of members of the family Coronaviridae include coronavirus and togovirus. Examples of coronaviruses include, but are not limited to, porcine epidemic diarrhea virus, porcine coronavirus (transmissible gastroenteritis coronavirus), bovine coronavirus, feline coronavirus, canine coronavirus, and human coronaviruses.

Other viruses include a member of the family Orthomyxoviridae. Members of the family Orthomyxoviridae include Influenzavirus A, Influenzavirus B, and Influenzavirus C. The influenza virus may be adapted to one or more hosts, including a mammal or a bird (avian influenza virus). Examples of mammals include, but are not limited to, a human (human influenza virus), and a pig (swine influenza virus).

Other viruses include a member of the family Adenoviridae. Members of the family Adenoviridae include members of the genus *Mastedenovirus*, which includes human adenoviruses. Other examples of viruses include Newcastle disease virus and bovine viral diarrhea virus.

A composition described herein may also be administered to a subject in need thereof in combination with other therapeutic compounds to increase the overall therapeutic effect. Therapeutic compounds useful for the treatment of an infection vary depending upon the infectious agent, and such therapeutic compounds are known and routinely used.

The present invention is illustrated by the following examples. It is to be understood that the particular examples, materials, amounts, and procedures are to be interpreted broadly in accordance with the scope and spirit of the invention as set forth herein.

EXAMPLE 1

Mature Gilts Experimentally Infected with PRRS Show Positive Responses to Dietary Inclusion of Insulin-like Growth Factor The following trial was conducted to evaluate the effects of feeding a composition that includes active IGF-1 to mature gilts on virus load and immune responses during PRRS challenge. Twenty mature gilts were divided equally into two groups, a control group and a test group. The gilts were at least 125 kilograms in body weight, and were negative for Porcine reproductive and respiratory syndrome virus (PRRSV). Gilts were selected to provide a model system for sows, and were obtained from the same farm to minimize variation. The trial started by feeding the test group a standard sow gestation diet supplemented with betaGRO, a composition that contained active IGF-1. The sow gestation diet supplemented with betaGRO at a concentration that resulted in ingestion of between 300 ng active IGF/kg bodyweight and 650 ng active IGF/kg bodyweight over 43 days. The standard sow gestation diet was supplemented with the composition at 4 lbs/ton. The control group was fed the same standard sow gestation diet without the supplement.

Twenty eight days after beginning the trial, all gilts were inoculated with PRRSV 1-8-4 USA strain (dose of $1 \times 10^5$ $TCID_{50}$, intramuscular administration of 3 mls to the neck). At the same day as the inoculation a blood sample was taken and the rectal temperature of each gilt was measured. Blood samples and rectal temperatures were also taken at 3 days and 15 days after inoculation.

Quantitative Real-Time PCR was used to measure the number of copies of viral RNA present in the blood. The results show that the test diet reduced the number of copies of viral RNA at 15 days-post-inoculation (dpi) by 86% over control pigs (p-value=0.02) (FIG. 1). There was a 98% reduction of the number of copies of viral RNA at 15-dpi versus 3-dpi in pigs fed active IGF (p-value <0.0001). These results have also been observed in sows administered the composition.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   administering a composition comprising active IGF to an animal, wherein the administering comprises daily administration of at least 5 nanograms of active IGF-1 per kilogram bodyweight of the animal, wherein the administering occurs before, during, and after the animal is exposed to an infectious agent, wherein the administering results in reducing the amount of infectious agent in the animal, wherein the infectious agent is a porcine reproductive and respiratory syndrome virus (PRRSV), and wherein the animal is a porcine species of post-weaning age.

2. The method of claim 1 wherein the administering comprises oral administration of the active IGF-1.

3. The method of claim 2 wherein the oral administration comprises administration of a feed to the animal, wherein the feed comprises the active IGF-1.

4. The method of claim 1 wherein the IGF-1 administered to the animal is obtained from a natural source.

5. The method of claim 4 wherein the natural source is blood or a blood-derived product.

6. The method of claim 4 wherein the natural source is milk or a milk-derived product.

7. The method of claim 4 wherein the natural source is colostrum or a colostrum-derived product.

8. The method of claim 1 wherein the composition further comprises inactive IGF-1.

9. The method of claim 1 wherein the animal is an adult.

* * * * *